United States Patent [19]

Lukas et al.

[11] Patent Number: 5,041,675

[45] Date of Patent: Aug. 20, 1991

[54] PROCESS FOR PREPARING 3(4),8(9)-BIS(AMINOMETHYL)-TRICYCLO(5.2.1.0$^{2,6}$) DECANE

[75] Inventors: Rainer Lukas, Essen; Klaus Mathieu; Franz Thönnessen, both of Oberhausen; Georg Dämbkes, Dinslaken; Hanswilhelm Bach, Duisburg, all of Fed. Rep. of Germany

[73] Assignee: Hoechst Aktiengesellschaft, Fed. Rep. of Germany

[21] Appl. No.: 569,581

[22] Filed: Aug. 17, 1990

Related U.S. Application Data

[63] Continuation of Ser. No. 373,095, Jun. 28, 1989, abandoned.

[30] Foreign Application Priority Data

Jun. 30, 1988 [DE] Fed. Rep. of Germany ....... 3922038

[51] Int. Cl.$^5$ .......................................... C07C 209/16
[52] U.S. Cl. ..................................... 564/446; 564/445
[58] Field of Search ........................ 564/445, 446

[56] References Cited

U.S. PATENT DOCUMENTS

| | | | |
|---|---|---|---|
| 3,483,253 | 12/1969 | Adam et al. | 564/446 |
| 3,565,954 | 2/1971 | Bouniot | 564/446 |
| 3,597,438 | 8/1971 | Brake | 564/446 |
| 4,317,932 | 3/1982 | Jachimowicz | 564/446 |

FOREIGN PATENT DOCUMENTS 1170226 11/1969 United Kingdom .

*Primary Examiner*—Richard L. Raymond
*Assistant Examiner*—Brian Bembenick
*Attorney, Agent, or Firm*—Jordan B. Bierman

[57] ABSTRACT

This invention relates to a process for preparing 3(4),8(9)-bis(aminomethyl)tricyclo[5.2.1.0$^{2,6}$]decane. The starting material for the synthesis of this compound is dicyclopentadiene, which is hydroformylated in the presence of a rhodium compound and subjected to reductive amination without the hydroformylation catalyst being separated from the reaction mixture.

31 Claims, No Drawings

PROCESS FOR PREPARING 3(4),8(9)-BIS(AMINOMETHYL)-TRICYCLO(5.2.1.0$^{2,6}$) DECANE

This application is a continuation of application Ser. No. 07/373,095 filed 06/28/89 now abandoned.

This Application claims the priority of German Application P 38 22 038.5, filed June 30, 1988.

The invention relates to a process for preparing 3(4),8(9)-bis(aminomethyl)tricyco[5.2.1.0$^{2,6}$]decane (hereinafter TCD-diamine). TCD-diamine is used in numerous commercial syntheses as a valuable intermediate. Thus, it is, for example, used for recovering polyurethanes or as a hardener for resins.

The customary starting material for preparing TCD-diamine is dicyclopentadiene. This starting material is obtained by dimerising cyclopentadiene. Dimerisation takes place at room temperature and can be accelerated by catalysts. The dimeric cyclopentadiene is converted into the corresponding tricyclodecane dialdehyde (TCD-dial) by hydroformylation, i.e. by reaction with carbon monoxide and hydrogen in the presence of catalysts, e.g. cobalt or rhodium, which are used as finely distributed metals or as compounds. A suitable process is, for example, described in the British Patent 11 70 226.

The conversion of the TCD-dial into the TCD-diamine is performed in the known manner by reductive amination of the formyl groups. For this purpose the dialdehyde is treated with ammonia and hydrogen in the presence of a hydrogenation catalyst, optionally after previous reaction with a primary amine. Suitable reaction conditions are temperatures of 80° to 150° C. and pressures of 5 to 12 MPa. Nickel-based hydrogenation catalysts have proved valuable for this purpose.

A disadvantage of the known process is that considerable difficulties are encountered in separating the dialdehyde from the reaction product of hydroformylation because of the high reactivity of the dialdehydes. They not only react with each other (forming higher molecular weight secondary products), but also with other compounds contained in the reaction product and are thus lost for the desired reaction. Attempts have been made to eliminate this shortcoming inter alia by particularly mild distillation, e.g. thin-layer distillation, under reduced pressure. However, even the observance of such precautionary measures does not prevent the undesired side-reactions. Moreover, suitable distillation processes are costly and jeopardize the cost-effectiveness of the synthesis.

Therefore, the problem was to develop a process which makes it possible to produce high yields of TCD-diamine from dicyclopentadiene while avoiding the difficulties described above.

DESCRIPTION OF THE INVENTION

The solution, according to the invention, is a process for preparing TCD-diamine by the hydroformylation of dicyclopentadiene in the presence of rhodium catalysts to form a reaction mixture, and subsequent reaction of the resultant tricyclodecane dialdehyde with hydrogen and ammonia in the presence of a hydrogenation catalyst (reductive amination). Surprisingly, it has been found that, with the new process, it is not necessary to isolate the TCD-dial and remove the hydroformylation catalyst from the reaction mixture before reductive amination. This is true despite the fact that the hydroformylation catalyst favors the further reaction of the initially formed TCD-dial to produce higher molecular weight compounds.

The starting material for preparing TCD-diamine according to the present process is dicyclopentadiene. It can be used in its commercially available form, i.e. without prior purification; the reaction proceeds according to the following equation:

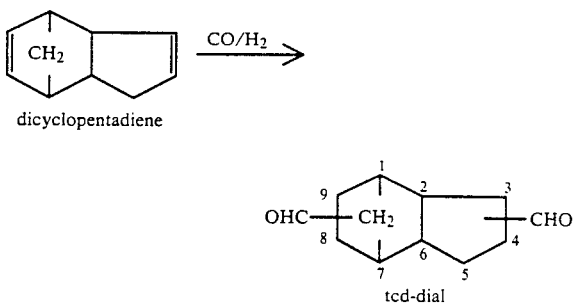

The hydroformylation of dicyclopentadiene with carbon monoxide and hydrogen takes place in the known manner in the presence of or in the absence of a solvent at temperatures of 100° to 200° C. and at pressures of 20 to 30 MPa. The reaction is performed in the presence of rhodium as a catalyst which can be used as a metal in finely divided form. However, preference is given to compounds such as dirhodium trioxide or rhodium salts of weak organic acids, e.g. of acetic acid or 2-ethylhexanoic acid. While the rhodium concentration can be varied between 20 and 100 mg of rhodium per kilogram of dicyclopentadiene, the preferred range is between 20 and 50 mg of Rh/kg of the diolefin. Hydroformylation is performed batchwise or preferably continuously.

Separation of the dialdehyde and/or removal of the catalyst, is not necessary. The hydroformylation mixture can be reductively aminated in the second reaction step just as it is formed, with or without a solvent.

The term reductive amination is to be understood as the reaction of the dialdehyde with hydrogen and ammonia in the presence of a hydrogenation catalyst, as shown below According to a preferred embodiment of this invention the dialdehyde is first reacted with a primary amine to form the corresponding diazomethine, then the diazomethine is treated with hydrogen and ammonia in the presence of a hydrogenation catalyst in accordance with the following equations:

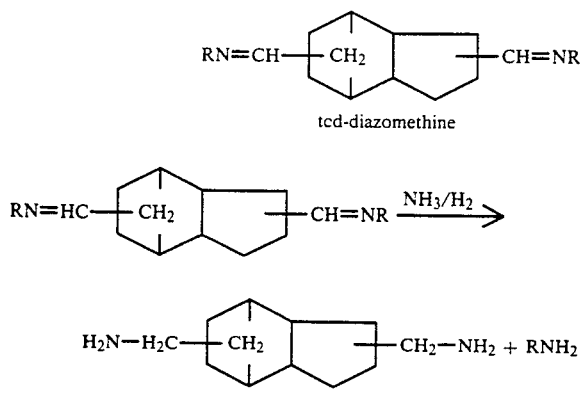

tcd-diazomethine

This reaction is also called reductive amination in the sense of this invention.

In order to form the diazomethine, 2 to 6 moles, in particular 3 to 4 moles, of a primary amine are added to the reaction mixture per mole of TCD-dial. The reaction between the starting materials takes place at room temperature; it can be accelerated by heating to 20° to 60° C., in particular 30° to 50° C. Amines having 2 to 10 carbon atoms in the molecule are suitable as primary amines. Particular success is obtained with amines having 3 to 6 carbon atoms in the molecule, most preferably n-butyl-amine.

The reductive amination of the dialdehyde or the diazomethine obtained from it is appropriately performed at temperatures of 80° to 150° C., preferably 120° to 140° C. The hydrogen pressure in the reactive vessel is 5 to 12 MPa and, in particular, 8 to 10 MPa at the reaction temperature.

Nickel or cobalt is used as the hydrogenation catalyst, either as Raney nickel or Raney cobalt, or also as the corresponding supported catalysts. A preferred catalyst contains 50 to 60% by weight of nickel or kieselguhr.

It is appropriate to use ammonia in excess. At least 2 moles of ammonia are required per formyl group or per diazomethine group. It is preferable to use 4 to 5 moles of ammonia per formyl or diazomethine group.

The reductive amination of the dialdehyde or the diazomethine can be performed in the absence of solvents, normally the final product acts itself as a solvent. With small discontinuous batches it is, however, advantageous to work with a solvent. Particularly good results are achieved when the solvent is tetrahydrofuran, isobutanol, butanol, or isopropanol.

Good yields of the mixture of isomeric diamines are obtained. Only a small amount of dialdehyde forms higher molecular weight condensation products. They are dissolved in the reaction mixture and do not interfere with the product being removed from the reactor and trouble-free handling of the raw products. The hydrogenation catalyst remains behind in the distillation residue, and the rhodium used in the hydroformylation stage precipitates out almost completely onto this catalyst. It can be removed by known methods.

In order to separate the isomeric TCD-diamines, the reaction mixture is distilled preferably under reduced pressure. The compounds are obtained as a colorless liquid which boils at about 310° C.

In the following examples, the new process is explained in more detail. Naturally, it is not intended to limit the invention to these special embodiments.

EXAMPLE 1

(a) Hydroformylation

In an autoclave equipped with a stirrer, a solution of 70 parts by weight of dicyclopentadiene in 30 parts by weight of toluene is heated to 135° C. Then synthesis gas ($H_2$: CO = 1 : 1) is fed into the solution at a pressure of 25 MPa in the presence of 50 ppm by weight of rhodium (as Rh-2-ethylhexanoate) over a period of three hours. The reaction product consists of 42% by weight of tricyclodecane dialdehyde, 44% by weight of toluene, the remainder being tricyclodecane monoaldehyde (11% by weight) and low and high-boiling components.

(b) Reductive Amination

In an autoclave, 30 parts by weight of the TDC-dial-containing hydrogenation raw product of (a) is added to 30 parts by weight of n-butylamine over a period of 1 hour, a maximum temperature of 60° C. being maintained. Then the mixture is stirred for another 30 minutes at 40° C. The reaction product containing the diazomethine of the TDC-dial and having a rhodium content of 18.5 ppm by weight is continuously hydrogenated in the presence of ammonia and hydrogen on a fixed-bed Raney nickel catalyst. The reaction takes place at a reaction temperature of 130° C., a hydrogen pressure of 8 MPa, an $NH_3$:diazomethine molar ratio of 50 : 1, and a space velocity of 0.4 volumes of product mixture per volume of catalyst per hour. After the $NH_3$ has been separated, the reaction product contains 27% by weight of TDC-diamine, 44% by weight of n-butylamine, 16% by weight of toluene, the remainder being isomers and afterrunnings. Then the product mixture is distilled to obtain the pure product. The amount of rhodium discharged from the hydrogenation reactor is 0.01 ppm by weight, i.e. 99.5% of the rhodium used is retained on the hydrogenation catalyst

EXAMPLE 2

Hydroformylation of dicyclopentadiene is performed as described in Example 1. After the first runnings have been separated by means of a thin-film evaporator, the hydroformylation product contains 74% by weight of TCD-dial and 37 mg of rhodium per kilogram of product.

30 parts by weight of hydroformylation product are continuously reacted with 30 parts by weight of n-butylamine in a reaction tube at 40° C. to form the corresponding diazomethine, the throughput being 0.2 volumes of product per reactor volume per hour. Then, at a temperature of 130° C., a hydrogen pressure of 8 MPa, an $NH_3$:diazomethine molar ratio of 10 : 1, and a space velocity of 0.3 volumes of product mixture per volume of catalyst per hour, the diazomethine is reacted continuously on a nickel catalyst to form TCD-diamine. The rhodium content in the reaction product is less than 0.1 ppm by weight. The TCD-diamine is purified by distillation.

What we claim is:

1. A process for the preparation of TCD-diamine comprising hydroformylation of dicyclopentadiene in the presence of at least one rhodium catalyst to form a hydroformylation product containing TCD-dial and, without removal of said rhodium catalyst, reaction of said TCD-dial in said hydroformylation product with hydrogen and ammonia in the presence of a hydrogenation catalyst (reductive amination) to form a reaction product containing said TCD-diamine.

2. The process of claim 1 wherein said TCD-dial in said hydroformylation product is first reacted with a primary amine to form a corresponding diazomethine and, thereafter, is treated with hydrogen and ammonia in the presence of a hydrogenation catalyst (reductive amination) to form a reaction product containing said TCD-diamine.

3. The process of claim 2 wherein there are 2 to 6 moles of said primary amine per mol of said TCD-dial.

4. The process of claim 3 wherein there are 3 to 4 moles of said primary amine per mol of said TCD-dial.

5. The process of claim 2 wherein said reaction between the TCD-dial with the primary amine takes place at temperature of at least room temperature.

6. The process of claim 5 wherein said temperature is 20° to 60° C.

7. The process of claim 6 wherein said temperature is 30° to 50° C.

8. The process of claim 2 wherein said primary amine has 2 to 10 carbon atoms.

9. The process of claim 8 wherein said primary amine has 3 to 6 carbon atoms.

10. The process of claim 9 wherein said primary amine is n-butyl amine.

11. The process of claim 1 wherein said reductive amination is carried out at a reductive amination temperature of 80° C. to 150° C.

12. The process of claim 11 wherein said reductive amination temperature is 120° to 140° C.

13. The process of claim 1 wherein said reductive amination is carried out at a hydrogen pressure of 5 to 12 MPa.

14. The process of claim 13 wherein said hydrogen pressure is 8 to 10 MPa.

15. The process of claim 2 wherein said reductive amination is carried out at a hydrogen pressure of 5 to 12 MPa.

16. The process of claim 15 wherein said hydrogen pressure is 8 to 10 MPa.

17. The process of claim 1 wherein said hydrogenation catalyst is Raney nickel and/or Raney cobalt.

18. The process of claim 17 wherein said hydrogenation catalyst is supported.

19. The process of claim 18 wherein said hydrogenation catalyst contains 50% to 60% by weight of Raney nickel and is on kieselguhr as a support.

20. The process of claim 2 wherein said hydrogenation catalyst is Raney nickel and/or Raney cobalt.

21. The process of claim 20 wherein said hydrogenation catalyst is supported.

22. The process of claim 21 wherein said hydrogenation catalyst contains 50% to 60% by weight of Raney nickel and is on kieselguhr as a support.

23. The process of claim 1 wherein there are at least 2 moles of said ammonia per formyl group.

24. The process of claim 23 wherein there are 4 to 5 moles of said ammonia per formyl group.

25. The process of claim 1 wherein said reductive amination is carried out in the presence of a solvent.

26. The process of claim 25 wherein said solvent is tetrahydrofuran, isobutanol, butanol, and/or isopropanol.

27. The process of claim 1 wherein said reductive amination product is distilled to separate isomeric TCD-diamines.

28. The process of claim 27 wherein said reductive amination product is distilled under reduced pressure.

29. The process of claim 1 wherein said hydroformylation takes place at 100° to 200° C. and under a pressure of 20 to 30 MPa.

30. The process of claim 29 wherein said rhodium catalyst has 20 to 100 mg of rhodium per kilogram of said dicyclopentadiene.

31. The process of claim 30 wherein there is 20 to 50 mg of said rhodium per kilogram of said dicyclopentadiene.

* * * * *